United States Patent
Deng et al.

(10) Patent No.: US 10,031,261 B2
(45) Date of Patent: Jul. 24, 2018

(54) METHOD FOR MEASURING X-RAY ENERGY OF AN ACCELERATOR IN AN INSPECTION SYSTEM

(71) Applicants: Tsinghua University, Beijing (CN); Nuctech Company Limited, Beijing (CN)

(72) Inventors: Yanli Deng, Beijing (CN); Qitian Miao, Beijing (CN); Junli Li, Beijing (CN); Guoping Zhu, Beijing (CN); Weiqiang Guan, Beijing (CN); Yuxin Hu, Beijing (CN); Shenjin Ming, Beijing (CN); Ming Huang, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 133 days.

(21) Appl. No.: 14/975,387

(22) Filed: Dec. 18, 2015

(65) Prior Publication Data
US 2016/0178795 A1    Jun. 23, 2016

(30) Foreign Application Priority Data
Dec. 18, 2014  (CN) .......................... 2014 1 0787025

(51) Int. Cl.
*G01D 18/00* (2006.01)
*G01V 13/00* (2006.01)
*G01N 23/083* (2018.01)

(52) U.S. Cl.
CPC ........... *G01V 13/00* (2013.01); *G01N 23/083* (2013.01); *G01N 2223/303* (2013.01)

(58) Field of Classification Search
CPC .. A61N 5/062; A61N 5/06; A61N 2005/1055; A61N 5/1045; A61N 5/1049;
(Continued)

(56) References Cited

U.S. PATENT DOCUMENTS 8,983,234 B2 *   3/2015  Holt ........................ G01J 3/28
                                                              382/294
2008/0226038 A1 * 9/2008  Fox ...................... A61B 6/4035
                                                              378/207
2011/0096906 A1 * 4/2011  Langeveld .......... G01N 23/063
                                                              378/82

FOREIGN PATENT DOCUMENTS

CN      102109605       6/2011
CN      103185891       7/2013
(Continued)

OTHER PUBLICATIONS

David et al., "Experimental and Monte Carlo-simulated spectra of standard mammography-quality beams" The British Journal of Radiology May 2012, pp. 629-635.
Monfared et al., "HVL evaluation of orthovoltage X-ray machine using EGSnrc code of simulation" International Journal of Radiation Research, Oct. 2014, pp. 325-330.
Verhaegen et al., "Monte Carlo modelling of radiotherapy kV x-ray units" Phys. Med. Biol, 44 (Mar. 1999), pp. 1767-1789.
(Continued)

*Primary Examiner* — Irakli Kiknadze
(74) *Attorney, Agent, or Firm* — Knobbe, Martens, Olson & Bear LLP

(57) ABSTRACT
The disclosure provides a method for measuring X-ray energy of an accelerator in an inspection system. the method comprises: building a database comprising correspondence between half-value layer (HVL) and energy under a predetermined condition; measuring HVL for X-rays of the accelerator in the inspection system on line under the same predetermined condition; and comparing the measured HVL with the HVLs in the database comprising correspondence between HVL and energy to determine the X-ray energy of the accelerator. The method is applicable to a large-scale container/vehicle inspection system for measurement of X-ray energy/HVL of the accelerator so as to acquire source state of the inspection system in real time.

20 Claims, 2 Drawing Sheets

(58) Field of Classification Search
CPC .......... A61N 5/1067; A61N 2005/0642; A61N 2005/0659; A61N 2005/0661; A61N 2005/0662; A61N 2005/1061; A61N 2005/1098; A61N 5/022; A61N 5/0618; A61N 5/0622; A61N 2005/1091; A61N 5/1017; A61N 2005/1059; A61N 2005/1072; A61N 5/103; A61N 5/1037; A61N 5/1064; A61N 2005/1094; A61N 2005/1087; A61N 2005/1088; A61N 5/1077; A61N 5/1001; A61N 5/1002; A61N 5/1048; A61N 5/1084; G01N 2223/303; G01N 23/083; G01N 2223/202; G01N 2223/501; G01N 2223/505; G01V 13/00; A61F 2009/00844; A61F 2009/00
USPC .................................. 378/4, 19, 64, 62, 207
See application file for complete search history.

(56) References Cited

FOREIGN PATENT DOCUMENTS

| | | |
|---|---|---|
| CN | 103645494 | 3/2014 |
| CN | 204009086 | 12/2014 |
| JP | S6443787 | 2/1989 |
| JP | H08304308 | 11/1996 |

OTHER PUBLICATIONS

Guoping et al., "New method for measuring x-ray energy of an accelerator—KD curve method", Beijing, China, pp. 1-7.
Chinese Office Action and Search Report for Chinese Application No. 201410787025.0 dated Dec. 18, 2014 (6 pgs), and English-language explanation/summary thereof (2 pgs); 8 pages total.
"Extended European Search Report received in Application No. 15200787.8, dated May 19, 2016"; 7 pgs.

* cited by examiner

METHOD FOR MEASURING X-RAY ENERGY OF AN ACCELERATOR IN AN INSPECTION SYSTEM

CROSS-REFERENCE TO RELATED APPLICATIONS

This application claims priority to Chinese Patent Application No. 201410787025.0, filed on Dec. 18, 2014, and entitled with "Method for Measuring X-ray Energy of an Accelerator in a Container Inspection System On Line", which is hereby incorporated by reference in its entirety.

FIELD

The disclosure relates to the technical field of rays measurement, in particular, to a method for measuring X-ray energy of an accelerator in an inspection system.

BACKGROUND

X-ray energy of an accelerator is an important source parameter for an inspection system and directly relates to radiography indexes and radiation protection performances of the inspection system. By measurement of X-ray energy of the accelerator, energy state of the accelerator can be acquired in real time, which can be used to direct adjustment of radiography indexes and radiation protection of the inspection system.

SUMMARY

In the application field of nuclear technology, the half-value layer (HVL) of X-rays is usually used to indicate X-ray energy of an accelerator. However, HVL measurement for X-rays generated by an accelerator is affected by many factors, for example, the width and depth of a collimator slit, the distance between a detector and a target spot, the distance between the detector and a shielding plate and the thickness of the shielding plate, etc. Thus, in practical measurement, the above detection conditions should be determined and a database comprising correspondence between HVL and energy should be built in order to calibrate X-ray energy of the accelerator. For energy measurement of an inspection system, the database comprising correspondence between HVL and energy should be built in connection with the structure of the inspection system and the characteristics of the detector. HVL of X-rays generated by the accelerator in the inspection system can be measured under the same conditions, and then X-ray energy of the accelerator could be acquired by reference to the database comprising correspondence between HVL and energy.

According to one aspect of the innovations herein, a method for measuring X-ray energy of an accelerator in an inspection system is provided to implement measurement of energy/HVL of X-rays generated by the accelerator and thereby to acquire source state of the inspection system in real time.

An illustrative method for measuring X-ray energy of an accelerator in an inspection system according to an embodiment of the disclosure may comprise steps including:

building a database comprising correspondence between HVL and energy under a predetermined condition;

measuring HVL of X-rays generated by the accelerator in the inspection system under the same predetermined condition; and comparing the measured HVL with HVLs in the database comprising correspondence between HVL and energy to determine X-ray energy of the accelerator.

DETAILED DESCRIPTION OF ILLUSTRATIVE IMPLEMENTATIONS

Illustrative systems and methods for measuring X-ray energy of an accelerator in an inspection system according to embodiments of the disclosure will be described in details in connection with appended drawings.

Figure 1:
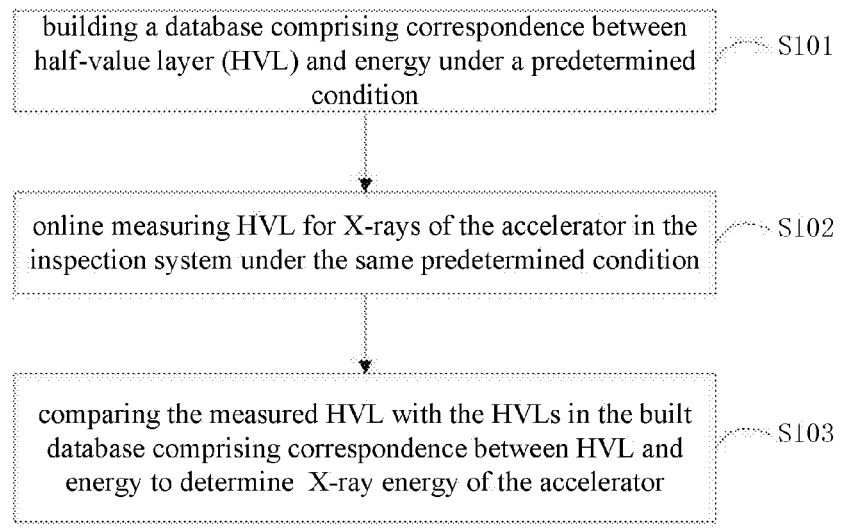
FIG. 1 is a flow diagram showing a method for measuring X-ray energy of an accelerator in an inspection system according to an embodiment of the disclosure.

FIG. 1 is a flow diagram showing a method for measuring X-ray energy of an accelerator in an inspection system according to an embodiment of the disclosure. As shown in FIG. 1, the method for measuring X-ray energy of an accelerator in an inspection system according to the embodiment of the disclosure comprises: step S101, building a database comprising correspondence between HVL and energy under a predetermined condition; step S102, measuring HVL for X-rays generated by the accelerator in the inspection system under the same predetermined condition; step S103, comparing the measured HVL with HVLs in the database comprising correspondence between HVL and energy to determine the X-ray energy of the accelerator.

In the step S101 of building the database comprising correspondence between HVL and energy, the database can be built based on simulation computation using Monte Carlo method or based on a standard accelerator measurement under a certain condition (i.e. the predetermined condition). The condition can be that the width and depth of the collimator slit of the accelerator, the distance between a detector and a target spot, the distance between a detector and a shielding plate and the thickness of the shielding plate are determined and fixed. In addition, the simulation computation or measurement of the database should be in connection with the inspection system, particularly the width and depth of the collimator slit of the accelerator, the distance between the detector and the target spot, the distance between the detector and the shielding plate and the thickness of the shielding plate, etc. In addition, the attenuation body used in the HVL measurement and the simulation computation can be made of any one of steel, lead, and tungsten. In addition, the attenuation body used in the HVL measurement and the simulation computation can be a single shielding plate with certain thickness or a combination of multiple shielding plates with respective thickness. That is, the required thickness of the attenuation body defined by HVL for X-ray intensity to be reduced by half can be calculated by directly measuring using a single shielding plate with a certain thickness, and can also be obtained by measuring intensity of X-rays which have passed through the multiple shielding plates and then performing fitting. These two ways yield different set of HVLs, so their scales for calibrating energy are different. Besides, the HVLs of the database can be the measurement data for the attenuation body being a single shielding plate with a certain thickness and can also be the combination of measurement data for multiple shielding plates with respective thickness. The combination of the measurement data for multiple shielding plates with respective thickness for the HVLs of the database can be performed by fitting.

After acquiring the database comprising correspondence between HVL and energy as said above, HVL for X-rays generated by the accelerator in the inspection system can be measured under the same predetermined condition.

In the step S102 of measuring the HVL, a detector used for measuring the HVL can be a detector owned by the inspection system or a detector additionally arranged to the inspection system. An attenuation body used for measuring the HVL can be a calibration device owned by the inspection system or an attenuation body additionally arranged to the inspection system. In addition, in the step of measuring HVL, it should be ensured that the relative position of the detector, the attenuation body and the target spot of the accelerator remain consistent with the one in the step of building the database. In addition, in the step of measuring HVL, it should be ensured that the material and size of the attenuation body remain consistent with those in the step of building the database. In addition, in the step of measuring HVL, it should be ensured that the width of the X-ray beam remains consistent with the one in the step of building the database. That is, the measurement condition in the step of measuring HVL must be the same with the condition used in the step of building the database comprising correspondence between HVL and energy.

In addition, in the step S103 of comparing the measured HVL with HVLs in the built database comprising correspondence between HVL and energy, the measured HVL and HVLs in the database built under the same measurement condition are compared to determine X-ray energy of the accelerator by reference to the HVL-energy correspondence of the database.

In the following, a process of measuring X-ray energy of an accelerator by using an attenuation body being a single shielding plate with certain thickness according to an embodiment of the disclosure is described.

Under a certain condition, for example, the width and depth of the collimator slit of the accelerator, the distance between the detector and the target spot, the distance between the detector and the shielding plate and the thickness of the shielding plate have been determined, for example, the accelerator is a 6/3 MV accelerator, the width and depth of the collimator slit are 2.3 mm and 170 mm respectively, the distance between the detector and the target spot is 1.5 m, the distance between the detector and the shielding plate is 300 mm, the thickness of the shielding plate is 125 mm and the area of the shielding plate is 300 mm×300 mm, a database comprising correspondence between HVL and energy could be computed based on simulation computation using Monte Carlo method or based on a standard accelerator measurement.

Figure 2:
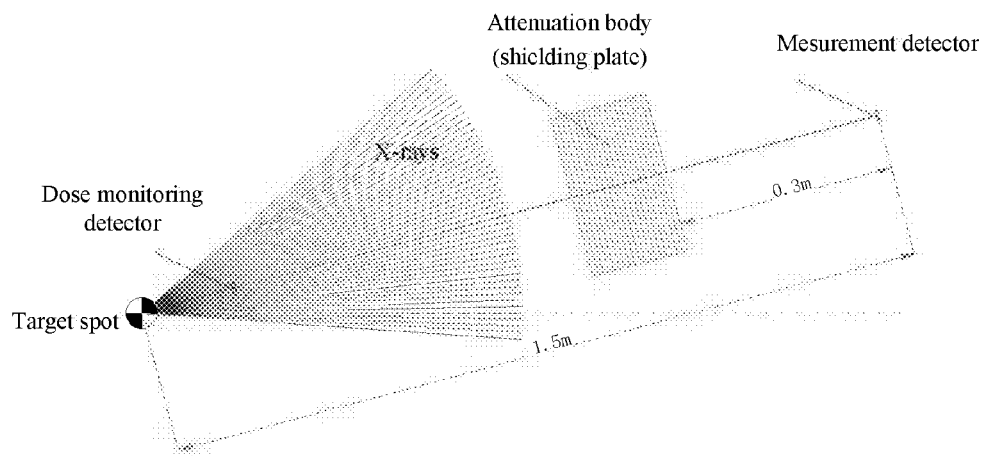
FIG. 2 is schematic diagram showing relative position of various components of the inspection system during measurement of HVL according to an embodiment of the disclosure.

In addition, FIG. 2 is schematic diagram showing relative position of various components in the inspection system during measurement of HVL according to an embodiment of the invention. As shown in FIG. 2, the target spot of the accelerator, the dose monitoring detector, the attenuation body (the shielding plate) and the measurement detector are placed in the order, and the parameters, for example, the width and depth of the collimator slit, the opening angle of the X-ray beam, the distance (1.5 m) between the detector and the target spot, the distance (300 mm) between the detector and the shielding plate and the thickness of the shielding plate, etc, as the detection condition, can be set, measured and recorded. That is, a measurement will be performed under the determined parameters. it should be noted that these parameters must be the same with those used in the step of—building the database comprising correspondence between HVL and energy in advance (i.e. the condition of the measurement is the same with the condition of building the database comprising correspondence between HVL and energy).

During measurement, with the accelerator emerging a beam normally without placing the shielding plate, vertical and horizontal position of measurement detector is adjusted to find a position at which the dose rate is the maximum. The measurement detector is fixed in this position. The dose rate D0 read by the measurement detector and the dose rate Dm0 read by the dose monitoring detector are recorded. It should be noted that the position of the measurement detector stays the same during the whole detection procedure.

A shielding plate is then placed between the target spot and the measurement detector. In an embodiment, the thickness T of the shielding plate placed between the target spot and the measurement detector is 125 mm. With the accelerator emerging a beam with a stable dose rate, the dose rate D1 read by the measurement detector and the dose rate Dm1 read by the dose monitoring detector are recorded.

HVL can be calculated using an equation (1) below, $$HVL = T/\log\left(\frac{D_0 \cdot D_{m1}}{D_1 \cdot D_{m0}}, 2\right) \quad (1)$$

Figure 3:
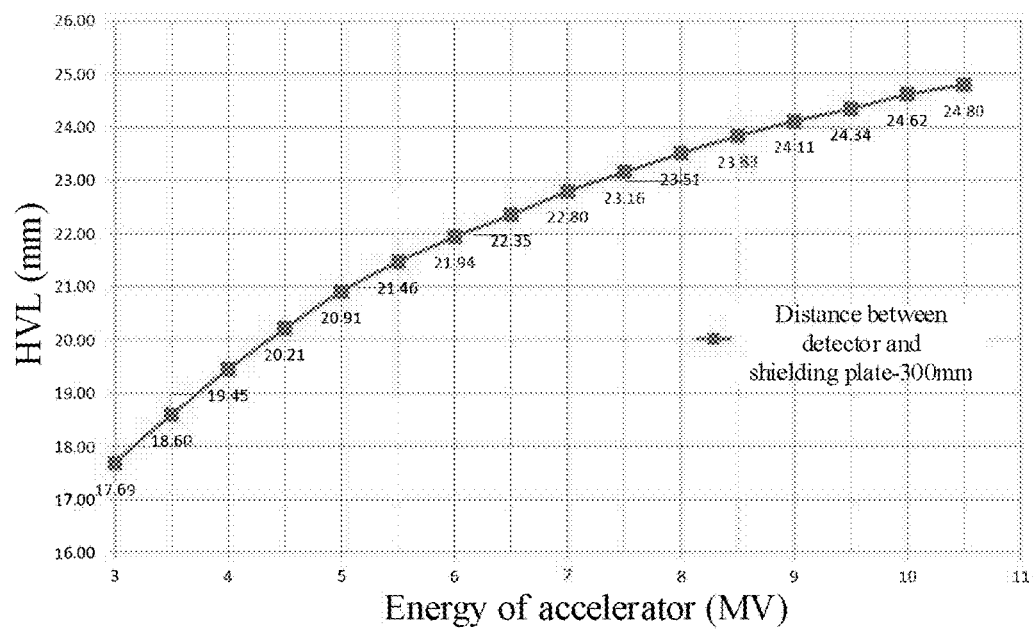
FIG. 3 is an exemplary diagram showing the database comprising correspondence between HVL and energy according to an embodiment of the disclosure.

The calculated HVL, for example, 22.0 mm, is compared with the HVLs in the database comprising correspondence between HVL and energy obtained in advance. FIG. 3 is an exemplary diagram showing the database comprising correspondence between HVL and energy according to an embodiment of the invention. As shown in FIG. 3, it can be obtained that the energy of the accelerator under the detection condition is about 6 MV for the HVL being 22.0 mm, for example. Thus, the measurement of X-ray energy of the accelerator in the inspection system has been completed.

The method for measuring X-ray energy of an accelerator in an inspection system according to the embodiment of the disclosure can be used in a container/vehicle inspection system, but is not limited to the container inspection system. The method according to the embodiments of the disclosure can be used in any case where X-ray energy needs to be detected.

According to the method of embodiments of the disclosure, the working state of the accelerator can be acquired in real time, which can be used to direct adjustment of performance indexes of the inspection system and to make the system more effective. Furthermore, according to the method of embodiments of the disclosure, HVL measurement can be performed directly using the detector and the calibration device owned by the inspection system, and thus for a dual energy inspection system, the measurement can be done without adding additional devices. Moreover, according the method of embodiment of the disclosure, the measurement for X-ray energy can be done by using an attenuation body being a single shielding plate with certain thickness, and thus it is convenient and time and effort saving for an inspection system having no calibration device to conduct X-ray energy measurement.

The above described embodiments are merely illustrative embodiments of the invention, but not intended to limit the invention. Any modifications, equivalent alternations and improvements that are made within the scope of the invention should be included in the protection scope of the invention.

What is claimed is:

1. A method for measuring X-ray energy of an accelerator in an inspection system, the method comprising:
    building a database comprising correspondence between half-value layer (HVL) and X-ray energy under a predetermined condition;
    measuring HVL for X-rays of the accelerator in the inspection system on line under the same predetermined condition; and
    comparing the measured HVL with HVLs in the database comprising correspondence between HVL and X-ray energy to determine the X-ray energy of the accelerator.

2. The method of claim 1, wherein the database is built based on simulation computation using Monte Carlo method.

3. The method of claim 1, wherein the database is built based on a standard accelerator measurement.

4. The method of claim 1, wherein the predetermined condition is that a width and depth of collimator slit of the accelerator, a distance between a detector and a target spot, distance between the detector and a shielding plate and a thickness of the shielding plate are determined and fixed.

5. The method of claim 4, wherein, in the step of building the database comprising correspondence between HVL and X-ray energy, an attenuation body being used is formed of any one of steel, lead, and tungsten.

6. The method of claim 5, wherein, in the step of building the database comprising correspondence between HVL and X-ray energy, an attenuation body being used includes a single shielding plate with a certain thickness.

7. The method of claim 6, wherein, in the step of building the database comprising correspondence between HVL and X-ray energy, an attenuation body being used includes a combination of multiple shielding plates with respective thickness.

8. The method of claim 5, wherein the step of measuring HVL includes using a detector associated with or contained within the inspection system.

9. The method of claim 5, wherein, in the step of measuring HVL, a detector being used is a detector additionally arranged to the inspection system.

10. The method of claim 4, wherein the step of measuring HVL comprises using an attenuation body that includes a calibration device associated with the inspection system.

11. The method of claim 10 wherein the attenuation body is formed of any one of steel, lead, and tungsten.

12. The method of claim 11, wherein the attenuation body is a single shielding plate with a certain thickness.

13. The method of claim 11, wherein the attenuation body is a combination of multiple shielding plates with respective thickness.

14. The method of claim 1, wherein, in the step of building the database comprising correspondence between HVL and X-ray energy, an attenuation body being used is formed of any one of steel, lead, and tungsten.

15. The method of claim 1, wherein, in the step of building the database comprising correspondence between HVL and X-ray energy, an attenuation body being used is a single shielding plate with a certain thickness.

16. The method of claim 1, wherein, in the step of building the database comprising correspondence between HVL and X-ray energy, an attenuation body being used is a combination of multiple shielding plates with respective thickness.

17. The method of claim 1, wherein the step of measuring HVL includes using a detector associated with or contained within the inspection system.

18. The method of claim 1, wherein, in the step of measuring HVL, a detector being used is a detector additionally arranged to the inspection system.

19. The method of claim 1, wherein the step of measuring HVL comprises using an attenuation body that includes a calibration device associated with the inspection system or an attenuation body additionally arranged to the inspection system.

20. The method of claim 1, wherein the step of measuring HVL includes using an attenuation body associated with or coupled to the inspection system.

* * * * *